(12) United States Patent
Prueksaritanont

(10) Patent No.: US 7,407,772 B2
(45) Date of Patent: Aug. 5, 2008

(54) SCREENING AND SELECTION METHODS FOR STATIN DRUG COMBINATIONS

(75) Inventor: Thomayant Prueksaritanont, Lansdale, PA (US)

(73) Assignee: Merck & Co., Inc., Rahway, NJ (US)

( * ) Notice: Subject to any disclaimer, the term of this patent is extended or adjusted under 35 U.S.C. 154(b) by 474 days.

(21) Appl. No.: 10/490,462

(22) PCT Filed: Sep. 20, 2002

(86) PCT No.: PCT/US02/30004

§ 371 (c)(1),
(2), (4) Date: Mar. 23, 2004

(87) PCT Pub. No.: WO03/026573

PCT Pub. Date: Apr. 3, 2003

(65) Prior Publication Data

US 2004/0180392 A1    Sep. 16, 2004

Related U.S. Application Data

(60) Provisional application No. 60/378,612, filed on May 7, 2002, provisional application No. 60/324,485, filed on Sep. 24, 2001.

(51) Int. Cl.
*C12Q 1/48* (2006.01)
(52) U.S. Cl. .................................................. 435/15
(58) Field of Classification Search ............... 435/15
See application file for complete search history.

(56) References Cited

U.S. PATENT DOCUMENTS 6,319,678 B1 * 11/2001 Trubetskoy et al. ............ 435/15

FOREIGN PATENT DOCUMENTS

WO        WO 02/058732          8/2002

OTHER PUBLICATIONS

Kojima J et al (1999) Identification of metabolites of NK-104, an HMG-CoA reductase inhibitor, in rat, rabbit and dog bile. Biol Pharm Bull, vol. 22, No. 2, pp. 142-150.*
Prueksaritanont, et al., Mechanistic Studies on Metabolic Interactions between Gemfibrozil and Statins; The Journal of Pharmacology and Experimental Therapeutics, vol. 301, No. 3; pp. 1042-1051, 2002.

Physician's Deck Reference, online version, printed Jul. 28, 2004, for ZOCOR, pp. 1, 8, 10, 16, and 17 of 20.
Prueksaritanont, et al., Effects of Fibrates on Metabolism of Statins in Human Hepatocytes; Drug Metabolism and Disposition, vol. 30, No. 11; pp. 1280-1287, 2002.
Jamal, et al., Rhabdomyolysis Associated With Hydroxymethylglutaryl-coenzyme A Reductase Inhibitors; American Heart Journal; vol. 147, No. 6, pp. 956-965, 2004.
Prueksaritanont, et al., Glucuronidation of Statins in Animals and Humans: A Novel Mechanism of Statin Lactonization; Drug Metabolism and Disposition; vol. 30, No. 5, pp. 505-512, 2002.
Everett, et al, Biotransformation of Pravastatin Sodium in Humans; Drug Metabolism and Diposition; vol. 19, No. 4, pp. 740-748, 1991.
Mercenne, et al, Effects of simvastatin, a lipoprotein-lowering drug, on the hepatic enzymes involved in drug metabolism in the Wistar rat; Xenobiotica, vol. 21, No. 7, pp. 859-864, 1991.
Uchiyama, et al, Metabolic fate of 2,2,-dimethylbutyryl moiety of simvastatin in rats: Identificatin of metabolites by gas chromatography/mass spectrometry; European Journal of Drug Metabolism and Pharmacokinetics, vol. 16, No. 3, pp. 189-196, 1991.
Dain, et al, Biotransformation of Fluvastatin Sodium in Humans; Drug Metabolism and Disposition, vol. 21, No. 4, pp. 567-572, 1993.
Halpin, et al, Biotransformation of Lovastatin; Drug Metabolism and Disposition, vol. 21, No. 6, pp. 1003-1011, 1993.
Boberg, et al, Biotransformation of Cerivastatin in Mice, Rats, and Dogs In Vivo; Drug Metabolism and Disposition, vol. 26, No. 7, pp. 640-652, 1998.
Black, et al, Metabolism and Excretion of Atorvastatin in Rats and Dogs; Drug Metabolism and Disposition, vol. 27, No. 8, pp. 916-923, 1999.
Evans, et al, The Myotoxicity of Statins; Current Opinion in Lipidology, vol. 13, No. 4, pp. 415-420, Aug. 2002.
Davidson, Michael, Combination Therapy for Dyslipidemia: Safety and Regulatory Considerations; The American Journal of Cardiology, vol. 90, No. 10B, pp. 50K-60K, Nov. 20, 2002.
Fujino, et al, Metabolic fate of pitavastatin, a new inhibitor of HMG-CoA reductase: human UDP-glucuronosyltransferase enzymes involved in lactonization; Xenobiotica, vol. 33, No. 1, pp. 27-41, 2003. (published online Jan. 1, 2003).

* cited by examiner

*Primary Examiner*—Jon Weber
*Assistant Examiner*—Kailash Srivastava
(74) *Attorney, Agent, or Firm*—Carol S. Quagliato; Mark R. Daniel

(57) ABSTRACT

A method for screening statins in their open acid form to determine the susceptibility of each tested statin to metabolic glucuronidation is provided. Also provided is a method for determining if a non-statin pharmaceutical drug co-administered with a statin that is susceptible to metabolic glucuronidation in its open acid form, will inhibit the glucuronidation of the statin and thereby increase the risk of an adverse drug interaction.

14 Claims, 6 Drawing Sheets

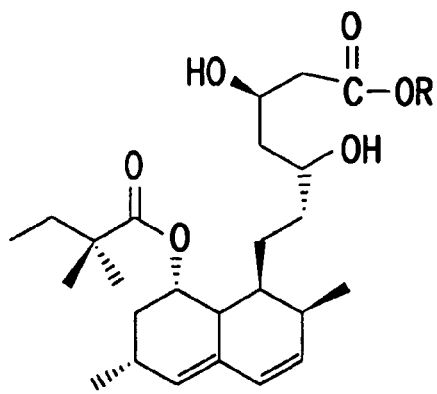
FIG.10A
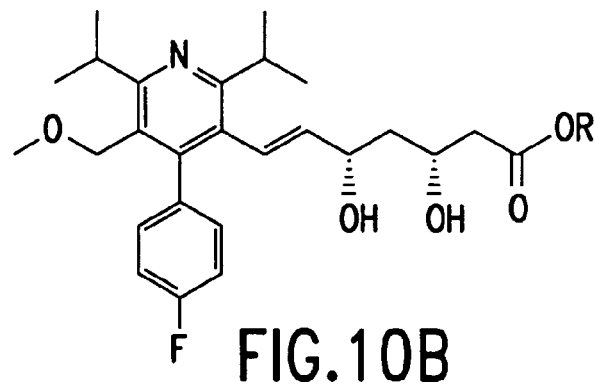
FIG.10B
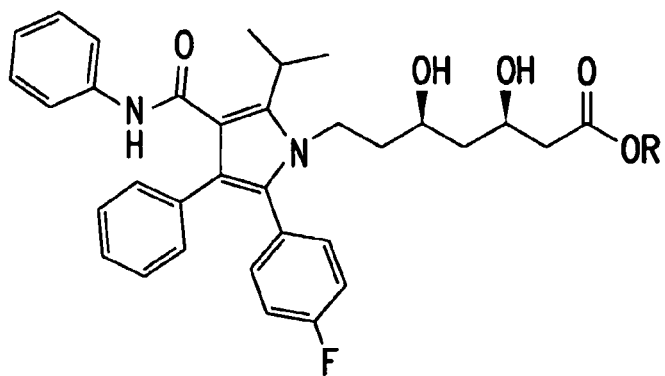
FIG.10C
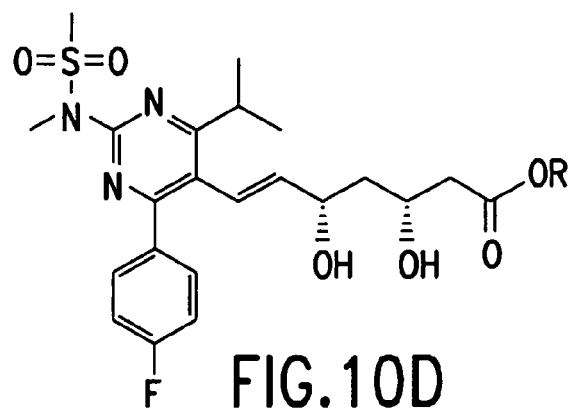
FIG.10D
R = H, PARENT STATIN HYDROXY ACID
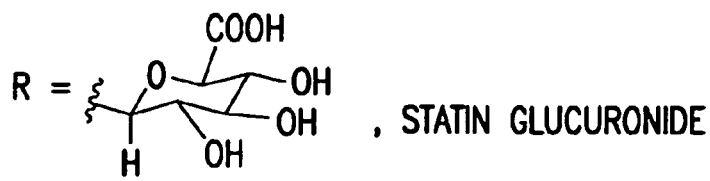, STATIN GLUCURONIDE

SCREENING AND SELECTION METHODS FOR STATIN DRUG COMBINATIONS

CROSS REFERENCE TO RELATED APPLICATIONS

This application is a 35 U.S.C. § 371 filing from International Application No. PCT/US02/30004, filed Sep. 20, 2002, which claims priority to U.S. Provisional Application No. 60/378,612, filed May 7, 2002, and to U.S. Provisional Application No. 60/324,485, filed Sep. 24, 2001.

BACKGROUND OF THE INVENTION

It has been clear for several decades that elevated blood cholesterol is a major risk factor for coronary heart disease (CHD), and many studies have shown that the risk of CHD events can be reduced by lipid-lowering therapy. Prior to 1987, the lipid-lowering armamentarium was limited essentially to a low saturated fat and cholesterol diet, the bile acid sequestrants (cholestyramine and colestipol), nicotinic acid (niacin), the fibrates and probucol. Unfortunately, all of these treatments have limited efficacy or tolerability, or both. With the introduction of lovastatin (MEVACOR®; see U.S. Pat. No. 4,231,938), the first inhibitor of HMG-CoA reductase to become available for prescription in 1987, for the first time physicians were able to obtain comparatively large reductions in plasma cholesterol with very few adverse effects.

In addition to the natural product lovastatin, there have been several semi-synthetic and totally synthetic HMG-CoA reductase inhibitors approved for prescription use, including simvastatin (ZOCOR®; see U.S. Pat. No. 4,444,784), pravastatin sodium salt (PRAVACHOL®; see U.S. Pat. No. 4,346,227), fluvastatin sodium salt (LESCOL®; see U.S. Pat. No. 5,354,772), atorvastatin calcium salt (LIPITOR®; see U.S. Pat. No. 5,273,995) and cerivastatin sodium salt (BAYCOL®; see U.S. Pat. No. 5,177,080). Still other HMG-CoA reductase inhibitors are known to be in development, for example pitavastatin also referred to as NK-104 (see PCT international publication number WO 97/23200); and rosuvastatin also known as ZD-4522 (CRESTOR®; see U.S. Pat. No. 5,260,440, and Drugs of the Future, 1999, 24(5), pp. 511-513). The structural formulas of these and additional HMG-CoA reductase inhibitors, are described at page 87 of M. Yalpani, "Cholesterol Lowering Drugs", Chemistry & Industry, pp. 85-89 (5 Feb. 1996). The HMG-CoA reductase inhibitors described above belong to a structural class of compounds which contain a moiety which can exist as either a 3-hydroxy lactone ring or as the corresponding ring opened dihydroxy open-acid, and are often referred to as "statins." An illustration of the lactone portion of a statin and its corresponding open-acid form is shown below.

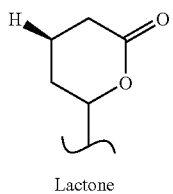

Lactone

-continued

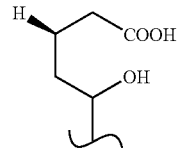

Dihydroxy Open-Acid

Salts of the dihydroxy open-acid can be prepared, and in fact, as noted above, several of the marketed statins are administered as the dihydroxy open acid salt forms. Lovastatin and simvastatin are marketed worldwide in their lactonized form. Lovastatin is shown as structural formula I, and simvastatin is shown as structural formula II, below.

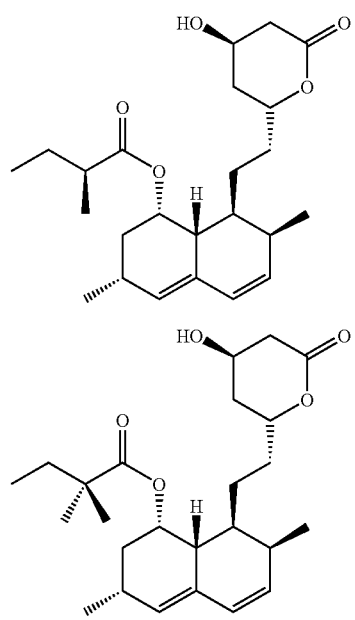

The lactonized forms of the statins are not active inhibitors of HMG-CoA reductase, but the dihydroxy open acid forms are. It is known that condensation of the dihydroxy open acid form of statins to the corresponding lactonized form occurs under acidic conditions, that is at about pH 4 or under. Therefore, due to the low gastric pH of the stomach, a statin conventionally administered by oral dosing in its lactone form will remain largely in its lactone form in the stomach. The vast majority of the drug will still be in the lactone form at the time of absorption from the intestine following oral dosing with the lactone. After absorption, the lactone enters the liver and it is in the hepatocytes that the lactone can be metabolized to the active open acid form, a reaction catalyzed by two hepatic esterases or "lactonases," one which is in the cytosolic and the other in the microsomal fraction. Once in the blood there is an additional plasma esterase that can also hydrolyze the lactone to the open acid. There may be some minimal chemical, i.e., non-enzymatic, hydrolysis that occurs in blood or in the liver; however, at the pH in blood and liver, there should not be any lactonization, i.e., conversion of open acid back to the lactone.

Since becoming available, millions of doses of simvastatin have been administered and these drugs have developed an excellent safety record. In fact, simvastatin has been administered to over 20 million patients worldwide in the past 11 years and has been demonstrated to be remarkably safe. However, as noted in the Physician's Desk Reference (PDR), occasional instances of myopathy have been associated with the use of all statins, including simvastatin, which manifest as muscle pain or weakness associated with grossly elevated creatine kinase, and more rarely instances of rhabdomyolysis have been reported, marked by the destruction of muscle cells which enter the bloodstream. The mechanism for statin-related myopathy is currently poorly understood. The risk of myopathy may be increased by high levels of HMG-CoA reductase inhibitory activity in plasma. It is known that many drugs, including certain statins such as simvastatin, are metabolised in the liver and intestine by the cytochrome P450 isoform 3A4 (CYP3A4) enzyme system. The very low risk of myopathy may be increased when a CYP3A4-metabolized statin is used in combination with a potent inhibitor of this metabolic pathway which can raise the plasma levels of HMG-CoA reductase inhibitory activity. Such potent inhibitors include cyclosporine; the azole antifungals, itraconazole and ketoconazole; the macrolide antibiotics, erythromycin and clarithromycin; HIV protease inhibitors; the antidepressant nefazodone; and large quantities of grapefruit juice (>1 quart daily).

It is also known that concomitant drug therapy with simvastatin and gemfibrozil, a member of the class of fibric acid derivatives (fibrates) which shows only minimal inhibition of in vitro CYP3A4 functional activity, increases the risk for myopathy. In a study involving combination treatment with simvastatin and gemfibrozil described in Backman, et al., Plasma concentrations of active simvastatin acid are increased by gemfibrozil, Clin. Pharmacology & Therapeutics, vol 68:2, 122-129 (August 2000), it was reported that gemfibrozil considerably increased plasma concentrations of open acid simvastatin, with only minimal increase in the plasma AUC (area under the curve) of parent simvastatin. The paper also stated that gemfibrozil showed no appreciable inhibitory effect on CYP3A4 mediated 1'-hydroxylation of midazolam in human liver microsomes, an in vitro assay for determining hepatic CYP3A4 activity. Therefore, since gemfibrozil is not an inhibitor of CYP3A4 in vitro, yet it increases the plasma AUC of open acid simvastatin when co-administered with simvastatin, the pharmacokinetic interaction between the two drugs is most likely via another pathway distinct from the CYP3A4 pathway.

Although the rate of occurrence of myopathy is extremely low for most statins, cerivastatin, sold in the U.S. under the tradename BAYCOL®, was recently withdrawn from the worldwide market after being linked to significantly more fatal cases of rhabdomyolysis than the other available statins. The side effect was most likely to occur when BAYCOL® was given in high doses or when it was given with the cholesterol drug gemfibrozil.

While the overall safety record for simvastatin is exceptional, it would be desirable to further optimize the safe utilization of simvastatin as well as statins in general by reducing the potential for adverse drug interactions, when the statins are co-administered with one or more additional active agents. It would also be desirable to further reduce the already low rate of occurrence of myopathy and rhabdomyolysis associated with the use of most statins. Further, it would be useful to know how cerivastatin differs pharmacokinetically from other statins in this regard in order to have a better understanding of the mechanism for statin-related myopathy. Statins are among the most widely used drugs in the world, and therefore the benefit of any further optimization of their safety profile would be significant.

SUMMARY OF THE INVENTION

It has now been discovered that a pathway for metabolism and clearance of certain statins, including simvastatin, atorvastatin, rosuvastatin and cerivastatin, involves glucuronidation of the open acid form of the statin via the UDP-glucuronosyltransferase (UGT) enzyme pathway (see Annu. Rev. Pharmacol. Toxicol, 2000, 40: 581-616, incorporated by reference). Inhibition of glucuronidation of the open acid statin by another active agent which competitively binds to the glucuronidating enzyme can cause an increase in the plasma AUC (area under the curve) of the active open acid statin. It has further been discovered that various statins display differential susceptibility to drug interactions at the level of glucuronidation. Furthermore, various fibrates such as gemfibrozil, fenofibrate and bezafibrate exhibit differential effects on the glucuronidation of various statins.

Additionally, it has been discovered that, unlike simvastatin and atorvastatin, oxidative metabolism of cerivastatin was markedly inhibited by gemfibrozil. Therefore, the formation of both cerivastatin glucuronide and oxidative metabolites of cerivastatin were markedly inhibited by gemfibrozil. Thus, inhibition of the formation of oxidative metabolites of an open acid statin by another active agent which competitively binds to the oxidating enzyme can also contribute to an increase in the plasma AUC of the active open acid statin.

Accordingly, it is one object of the instant invention to provide a method for screening statins to determine the susceptibility of each tested statin for metabolic glucuronidation, and particularly to determine via which UGT isozymes the glucuronidation proceeds. More particularly, the invention provides a method for screening statins to determine the susceptibility of each tested statin for metabolic glucuronidation in addition to susceptibility for metabolic oxidation via a CYP isozyme.

It is another object to provide a method for determining if a non-statin pharmaceutical drug co-administered with a statin that is susceptible to metabolic glucuronidation to a patient in need thereof, will inhibit the glucuronidation of the statin and thereby increase the risk of adverse pharmacokinetic drug interaction. In particular, the non-statin is selected from a fibric acid derivative (fibrate) and a PPAR receptor agonist.

It is another object to provide a method for determining if a non-statin pharmaceutical drug co-administered to a patient in need thereof with a statin that is susceptible to metabolic oxidation, will inhibit the oxidation of the statin and thereby increase the risk of adverse pharmacokinetic drug interaction.

It is another object to provide a method for appropriately selecting a statin and a non-statin pharmaceutical drug that do not competitively bind to the same UGT isozyme or isozymes, particularly where the statin is metabolized via one or more of UGT1A1, UGT1A3 and UGT1A10, for co-administration to a patient in need of such co-administered drug treatment.

It is another object to provide a method for appropriately selecting a statin and a non-statin pharmaceutical drug that do not competitively bind to the same UGT isozyme or isozymes, particularly where the statin is metabolized via one or more of UGT1A1, UGT1A3 and UGT1A10, and further do not competitively bind to the same CYP isozyme, particularly where the statin is metabolized via CYP3A4 and/or CYP2C9, and more particularly where the statin is metabolized via one or more of CYP3A4, CYP2C9 and CYP2C8, for co-administration to a patient in need of such co-administered drug treatment.

It is another object to provide a method for avoiding or minimizing inhibition of the metabolic glucuronidation of a statin by a co-administered non-statin pharmaceutical drug, particularly a fibric acid derivative or a PPAR receptor agonist, wherein the statin is susceptible to said glucuronidation and is administered in its lactone or open acid form, comprising administering the statin and the co-administered drug only if the co-administered drug has an $IC_{50}$ value relative to the statin in the "glucuronidation inhibition assay" that is 5-fold or more greater than the maximum plasma concentration obtained following a daily therapeutic dose of the non-statin drug, or more particularly, an $IC_{50}>400$ μM in the "glucuronidation inhibition assay."

It is another object to provide a method for reducing the risk for an adverse drug interaction event, particularly myopathy and rhabdomyolysis, from co-administration of a statin with a non-statin pharmaceutical drug in a patient in need of said co-administration, as well as a method for avoiding or minimizing an increase in the plasma levels of open acid statin by a co-administered non-statin pharmaceutical drug in a patient in need of said co-administration, utilizing the methods further described herein. Additional objects will become evident from the following detailed description.

BRIF DESCRIPTION OF THE FIGURES

FIG. 10 shows the chemical structures of the hydroxy open-acid forms and the corresponding acyl glucuronide conjugates of (A) simvastatin, (B) cerivastatin, (C) atorvastatin and (D) rosuvastatin.

DETAILED DESCRIPTION OF THE INVENTION

Figure 1:
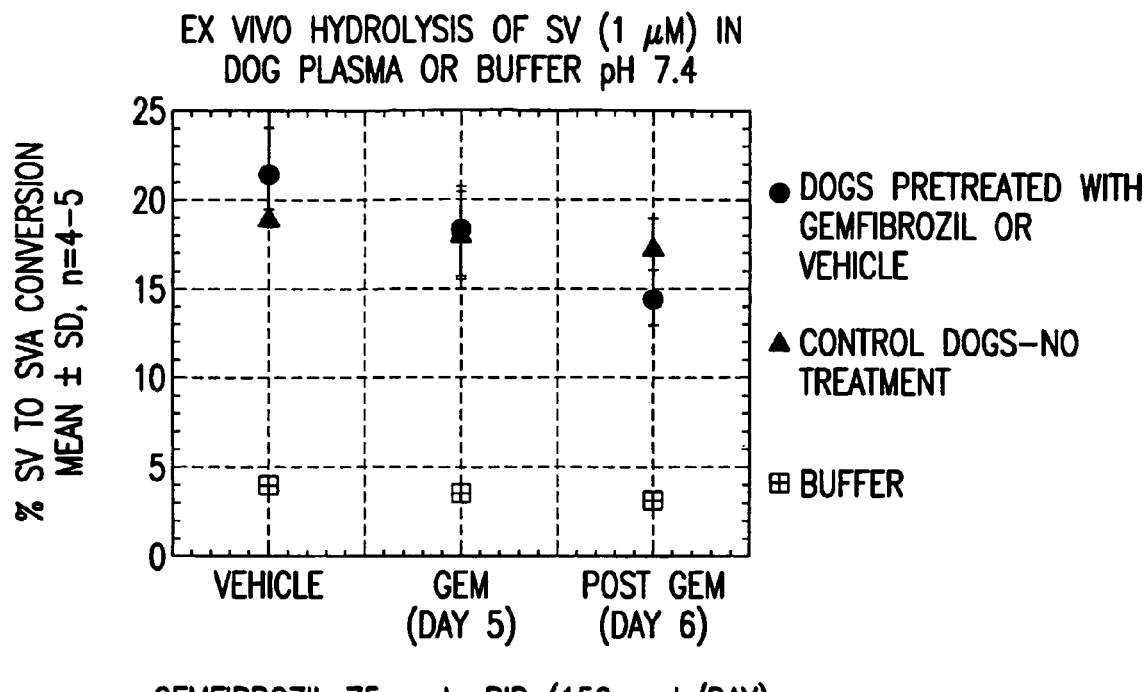
FIG. 1 shows the ex vivo hydrolysis of simvastatin (SV) by gemfibrozil in dogs over time.

Since both fibrates and statins can rarely cause myopathy when administered as monotherapy, it has been generally accepted that the observed increased risk of myopathy, including rhabdomyolysis, when these agents are co-administered is due primarily to a pharmacodynamic drug-drug interaction. Clinical pharmacokinetic studies have demonstrated a modest effect of multiple oral doses of gemfibrozil on the single oral dose plasma pharmacokinetics of simvastatin and lovastatin (Backman et al., Clin Pharmacol Ther 2000; 68: 122-129; Kyrklund et al., Clin Pharmacol Ther 2001;69:340-5). In particular, gemfibrozil led to a disproportionate effect on the plasma levels of the β-hydroxyacid metabolites of these two statins (increased AUC of simvastatin acid by 185% and increased AUC of lovastatin acid by 280%) with a minimal effect on plasma levels of simvastatin lactone (increased by 35%) and no significant effect on plasma levels of lovastatin lactone. These pharmacokinetic effects are modest suggesting that the substantial increase in the risk of myopathy when lovastatin and simvastatin are co-administered with gemfibrozil is due to a pharmacodynamic interaction; however, a contribution of the observed pharmacokinetic interaction cannot be excluded.

Gemfibrozil has been shown not to inhibit cytochrome P450 isoform 3A4 (CYP3A4), the pathway primarily responsible for the metabolism of both simvastatin and lovastatin. Therefore, the effect of gemfibrozil on the plasma pharmacokinetics of simvastatin and lovastatin must be mediated by a mechanism other than inhibition of CYP3A4.

We have now identified simvastatin acid glucuronide, shown as structure III below, as a novel metabolite of simvastatin acid in both animals (in vivo and in vitro) and humans (in vitro and in vivo).

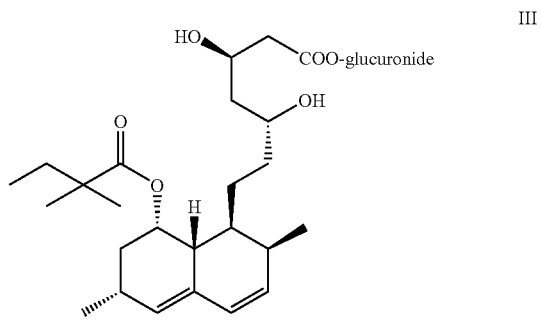

III

Our studies have provided evidence suggesting that the observed clinical effect of gemfibrozil on plasma levels of simvastatin acid may be mediated, at least in part, by its ability to inhibit the glucuronidation of simvastatin acid. Furthermore, these studies have also demonstrated that cerivastatin is uniquely susceptible to inhibition of glucuronidation by gemfibrozil and that gemfibrozil is a more potent inhibitor of statin acid glucuronidation than fenofibrate.

In addition, the oxidation of cerivastatin, which has been shown to be mediated by CYP3A4 and CYP2C8 (see Boberg et al., Drug Metab Dispos. 1997 March 25(3):321-31; Muck W., Clin Pharmacokinet. 2000 Aug, 39(2):99-116), was found to be markedly inhibited by gemfibrozil in human liver microsomes. Since gemfibrozil is not a potent inhibitor of CYP3A4, the observed inhibition of cerivastatin oxidative metabolism appears due to inhibition of CYP2C8 activity by gemfibrozil.

These preclinical studies focused on drug interactions mediated at the level of inhibition of glucuronidation of simvastatin acid, atorvastatin and cerivastatin by either gemfibrozil or fenofibrate. The results of these studies indicate that the various statins display differential susceptibility to drug interactions at the level of glucuronidation. Furthermore, gemfibrozil and fenofibrate exhibit differential effects on the glucuronidation of various statins.

Following oral administration of simvastatin (4 mg/kg P.O., single dose) to dogs pretreated with gemfibrozil (75 mg/kg P.O., bid for 5 days), both AUC and Cmax values of simvastatin acid, but not of simvastatin, were increased by about 3.5 fold and 2.6 fold, respectively. These results were similar to those reported in the clinical pharmacokinetic study in humans (Backman et al,—see above) who received gemfibrozil (600-mg tablet bid for 3 days) and simvastatin (40-mg tablet, single oral dose). Additional experiments revealed that gemfibrozil did not affect ex vivo simvastatin hydrolysis in dog plasma. However, gemfibrozil caused marked inhibition of simvastatin acid glucuronidation ($IC_{50}$=195 µM) in dog liver microsomes; in contrast gemfibrozil had a minimal effect on simvastatin acid oxidation ($IC_{50}$~1000 µM). In vivo experiments confirmed that gemfibrozil caused a significant decrease (~2-fold) in the plasma clearance of simvastatin acid and in the biliary excretion of simvastatin-glucuronide in dogs. Collectively, the results suggested that gemfibrozil-mediated elevations of simvastatin acid AUC following simvastatin administration to dogs were due, at least in part, to the inhibitory activity of gemfibrozil on simvastatin acid glucuronidation.

Further studies revealed that simvastatin acid also underwent glucuronidation in human liver microsomes and in vivo in humans following administration of radiolabeled simvastatin acid. The extent of glucuronidation of simvastatin acid in humans, both in vivo and in vitro, was less than that observed in dogs. In addition, gemfibrozil was found to cause a more pronounced inhibition of the glucuronidation of simvastatin acid ($IC_{50}$=354 µM) than CYP3A-mediated oxidative pathways ($IC_{50}$>800 µM), similar to the case in dogs. The glucuronidation of gemfibrozil and of simvastatin acid was catalyzed by at least two common human UGT isozymes (UGT1A1 and 1A3), and competitive inhibition by gemfibrozil on simvastatin acid glucuronidation was observed in human liver microsomes. Based on these results and the above findings in dogs, it is concluded that gemfibrozil-mediated elevations of simvastatin acid AUC following oral simvastatin administration to humans may be due, at least in part, to the inhibitory activity of gemfibrozil on simvastatin acid glucuronidation.

In subsequent studies, potential differences or similarities, in the metabolic interaction at the level of glucuronidation were assessed between various statins and gemfibrozil using in vitro approaches. In human liver microsomes, cerivastatin and atorvastatin, similar to simvastatin acid, formed an acyl glucuronide conjugate. Kinetic studies of statin glucuronidation in human liver microsomes showed that cerivastatin and atorvastatin underwent glucuronidation much faster than did simvastatin acid; the intrinsic clearance of glucuronidation of simvastatin acid, atorvastatin and cerivastatin were 0.4 µl/min/mg, 4.0 µl/min/mg and 2.9 µl/min/mg, respectively. Further studies revealed that the glucuronidation of cerivastatin was more susceptible to inhibition by gemfibrozil than was simvastatin acid or atorvastatin glucuronidation; the $IC_{50}$ values were 82 µM, 316 µM and 354 µM for cerivastatin, atorvastatin and simvastatin acid, respectively. These in vitro data suggest that cerivastatin is likely to be more susceptible than simvastatin acid or atorvastatin to interaction with gemfibrozil at the level of glucuronidation in humans.

Studies also were conducted to examine differences or similarities, in the inhibitory potential of fibrates on glucuronidation of statins in vitro. In human liver microsomes, gemfibrozil was more potent than fenofibrate as an inhibitor of glucuronidation of both simvastatin acid and of cerivastatin; the $IC_{50}$ values for inhibition of glucuronidation for simvastatin and cerivastatin were 354 µM and 82 µM for gemfibrozil and 682 µM and 433 µM for fenofibrate, respectively. In dog liver microsomes, gemfibrozil also was a more potent inhibitor of simvastatin acid glucuronidation ($IC_{50}$=195 µM) than was fenofibric acid ($IC_{50}$=283 µM). Consistent with this, fenofibrate had a minimal effect on the plasma clearance of simvastatin acid following intravenous administration of simvastatin acid to dogs, in contrast to gemfibrozil. Considering that the exposure to gemfibrozil in humans is >2-fold greater than exposure to fenofibrate/fenofibric acid at their respective therapeutic doses, these results suggest that in humans, gemfibrozil is more likely than fenofibrate to interact with cerivastatin, simvastatin acid, and atorvastatin at the level of glucuronidation.

In summary, our recent preclinical studies have demonstrated that:

1) the gemfibrozil-mediated elevations of simvastatin acid AUC following oral simvastatin administration to humans might be due, at least in part, to the inhibitory activity of gemfibrozil on simvastatin acid glucuronidation, 2) cerivastatin is likely to be more susceptible than simvastatin acid or atorvastatin to interaction with gemfibrozil at the level of glucuronidation in humans, and 3) gemfibrozil is more likely than fenofibrate to interact with cerivastatin, simvastatin acid, and/or atorvastatin at the level of glucuronidation.

Accordingly, one embodiment of the instant invention involves a method for appropriately selecting a statin and a non-statin drug for co-administration to a patient in need of such co-administered drug treatment, wherein the statin is susceptible to human metabolic glucuronidation by a UGT isozyme, comprising:
 (a) testing the statin in the UGT-specific glucuronidation assay to identify which one or more UGT isozymes are responsible for glucuronidation of the statin, and
 (b) selecting the non-statin as appropriate for co-administration with the statin if:
  (i) the non-statin is not metabolically glucuronidated as determined by testing the non-statin in the glucuronidation assay, or
  (ii) the non-statin is not metabolically glucuronidated by any of the one or more UGT isozymes identified in step (a) as determined by testing the non-statin in the UGT-specific glucuronidation assay.

Another aspect of this embodiment involves a method for appropriately selecting a statin and a non-statin drug that do not bind, either competitively or non-competitively, to one or more of the same human UGT isozymes for co-administration to a patient in need of such co-administered drug treatment, wherein the statin is susceptible to human metabolic glucuronidation by at least one UGT isozyme, comprising:
 (a) testing the non-statin in the glucuronidation inhibition assay to determine if the non-statin inhibits, either competitively or non-competitively, the metabolic glucuronidation of the statin; and
 (b) selecting the non-statin drug as appropriate for co-administration if it does not inhibit the metabolic glucuronidation of the statin.

Particularly, the statin and the non-statin drug do not competitively bind to one or more of the same human UGT isozymes, and in step (a), the non-statin is tested to determine if it competitively inhibits the metabolic glucuronidation of the statin.

In a second embodiment of this invention, a method is provided for avoiding or minimizing inhibition of the metabolic glucuronidation of a statin by a co-administered non-statin drug, comprising administering the statin and the non-statin drug only if the non-statin drug has an $IC_{50}$ value relative to the statin in the glucuronidation inhibition assay that is 5-fold or more greater than the maximum plasma concentration obtained following a daily therapeutic dose of the non-statin drug. So, for example, if the non-statin pharmaceutical drug has a peak plasma concentration in humans of about 10 μM after administration of a daily dose, then a 5-fold greater $IC_{50}$ value for that non-statin (relative to a given statin) would be an $IC_{50}$ of about 50 μM. Thus, in order to avoid or minimize inhibition of the metabolic glucuronidation of the statin, as well as to avoid or minimize an increase in the plasma levels of open-acid statin, reduce the risk for an adverse drug interaction, and appropriately select a statin and non-statin drug for adminstration to a patient in need thereof, the non-statin would only be selected for co-administration to the patient if its $IC_{50}$ was about 50 μM or greater relative to the statin in the glucuronidation inhibition assay.

In a third embodiment of this invention, the patient is administered the statin and the co-administered non-statin drug only if the co-administered drug has an $IC_{50}$ value relative to the statin in the glucuronidation inhibition assay that is 5-fold or more greater than the maximum plasma concentration obtained following a daily therapeutic dose of the non-statin drug.

In one aspect of the third embodiment, a method is provided for avoiding or minimizing an increase in the plasma levels of open acid statin by a co-administered non-statin drug, wherein the statin is metabolized by at least one human UGT isozyme and is administered in its lactone or open acid form to a patient in need of such co-administered drug treatment, comprising co-administering a non-statin drug that does not inhibit the same at least one UGT isozyme that the statin is metabolized by.

In another aspect of the third embodiment, a method is provided for avoiding or minimizing an increase in the plasma levels of open acid statin by a co-administered non-statin drug, wherein the statin is metabolized by at least one human UGT isozyme and by at least one CYP isozyme and is administered in its lactone or open acid form to a human in need of such co-administered drug treatment, comprising co-administering a non-statin drug that
  (a) has an $IC_{50}$ value relative to the statin in the glucuronidation inhibition assay that is 5-fold or more greater than the maximum plasma concentration obtained following a daily therapeutic dose of the non-statin drug, and
  (b) is not metabolized by the same at least one CYP isozyme as the statin, or
  (c) does not inhibit the same at least one CYP isozyme that metabolizes the statin.

In another aspect of this embodiment, a method is provided for avoiding or minimizing an increase in the plasma levels of open acid statin by a co-administered non-statin drug, wherein the statin is metabolized by at least one human UGT isozyme and by at least one CYP isozyme and is administered in its lactone or open acid form to a human in need of such co-administered drug treatment, comprising co-administering a non-statin drug that
  (a) does not inhibit the same at least one UGT isozyme that the statin is metabolized by, and
  (b) does not inhibit the same at least one CYP isozyme that the statin is metabolized by.

In a fourth embodiment of this invention, a method is provided for reducing the risk for an adverse drug interaction from co-administration of a statin with a non-statin pharmaceutical drug in a patient in need of said co-administration, wherein the statin is metabolized by at least one human UGT isozyme, comprising co-administering a non-statin drug that has an $IC_{50}$ value relative to the statin in the glucuronidation inhibition assay that is 5-fold or more greater than the maximum plasma concentration obtained following a daily therapeutic dose of the non-statin drug.

In an aspect of the fourth embodiment, the statin is additionally metabolized by at least one human CYP isozyme and
  (a) is not metabolized by the same at least one CYP isozyme that the statin is metabolized by, or
  (b) does not inhibit the same at least one CYP isozyme that the statin is metabolized by.

In a fifth embodiment of this invention, a method is provided for screening a statin to determine if it is potentially susceptible to an adverse pharmacokinetic drug interaction in a patient who is a co-administered a non-statin drug that is metabolically glucuronidated, comprising testing the statin in the glucuronidation assay to determine if the statin is metabolically glucuronidated.

In one aspect of this embodiment a method is provided for screening a statin to determine if it is susceptible to an adverse pharmacokinetic drug interaction in a human who is a co-administered a non-statin drug that is metabolically glucuronidated, comprising
  (a) testing the statin in the glucuronidation assay to determine if the statin is metabolically glucuronidated, and if so
  (b) testing the non-statin to determine the $IC_{50}$ of the non-statin relative to the statin in the glucuronidation inhibition assay; and
  (c) determining that the statin is not susceptible to an adverse pharmacokinetic drug interaction with the non-statin if the non-statin has an $IC_{50}$ value in the glucuronidation inhibition assay is 5-fold or more greater than the maximum plasma concentration obtained following a daily therapeutic dose of the non-statin drug.

In another aspect of the fifth embodiment, a method is provided for screening a statin to determine if human metabolic glucuronidation of the statin is susceptible to inhibition by a co-administered non-statin drug that is metabolically glucuronidated by UGT1A1, comprising testing the statin in the UGT-specific glucuronidation assay employing human recombinant UGT1A1 to determine if the statin is metabolically glucuronidated by UGT1A1.

In another aspect of the fifth embodiment, a method is provided for screening a statin to determine if human metabolic glucuronidation of the statin is susceptible to inhibition by a co-administered non-statin drug that is metabolically glucuronidated by UGT1A3, comprising testing the statin in the UGT-specific glucuronidation assay employing human recombinant UGT1A3 to determine if the statin is metabolically glucuronidated by UGT1A3.

In another aspect of the fifth embodiment, a method is provided for screening a statin to determine if human metabolic glucuronidation of the statin is susceptible to inhibition by a co-administered non-statin drug that is metabolically glucuronidated by UGT1A10, comprising testing the statin in the UGT-specific glucuronidation assay employing human recombinant UGT1A10 to determine if the statin is metabolically glucuronidated by UGT1 A10.

In a sixth embodiment of this invention, a method is provided for avoiding or minimizing inhibition of the metabolic oxidation of a statin by a co-administered non-statin pharmaceutical drug, wherein the statin is susceptible to said oxidation and is administered in its lactone or open acid form, comprising administering the statin and the co-administered drug only if the co-administered drug has an $IC_{50}$>100 μM relative to the statin in the "oxidation inhibition assay" for all of its oxidative metabolites.

In one aspect of this embodiment, the instant invention provides a method for reducing the risk for an adverse drug interaction from co-administration of a statin with a non-statin in a patient in need of said co-administration, wherein the statin is metabolized by at least one human UGT isozyme and is also susceptible to metabolic oxidation, comprising co-administering a non-statin drug that has (a) an $IC_{50}$ value relative to the statin in the glucuronidation inhibition assay that is 5-fold or more greater than the maximum plasma concentration obtained following a daily therapeutic dose of the non-statin drug, and (b) an $IC_{50} > 100$ μM relative to said statin in the oxidation inhibition assay.

As an additional example within all embodiments and aspects thereof described herein, the non-statin drug has an $IC_{50} > 400$ μM relative to the statin in the glucuronidation inhibition assay.

As an additional example within all embodiments and aspects thereof described herein, the UGT isozyme is selected from UGT1A1, UGT1A3 and UGT1A10.

As an additional example within all embodiments and aspects thereof described herein, the CYP isozyme is selected from CYP3A4, CYP2C9 and CYP2C8. More particularly, the isozyme is CYP3A4.

As an additional example within all embodiments and aspects thereof described herein, the statin is selected from simvastatin, open-acid simvastatin and the pharmaceutically acceptable salts thereof. As a further example within all embodiments and aspects thereof described herein, the non-statin drug is a PPAR receptor agonist, particularly a PPARγ agonist, a PPARα agonist such as a fibric acid derivative, or a PPAR dual α/γ agonist.

The terms "glucuronidation assay," "UGT-specific glucuronidation assay," "glucuronidation inhibition assay" and "oxidation inhibition assay" as used herein refer to specific assays as defined in the Examples, below.

HMG-CoA reductase inhibitors of the statin class are used with this invention. Compounds that have inhibitory activity for HMG-CoA reductase can be readily identified using assays well known in the art. For example, see the assays described or cited in U.S. Pat. No. 4,231,938 at col. 6, and WO 84/02131 at pp. 30-33, herein incorporated by reference.

In general, HMG-CoA reductase inhibitors belong to a structural class of compounds which contain a moiety which can exist as either a 3-hydroxy lactone ring or as the corresponding 3,5-dihydroxy open-acid, and are commonly referred to as "statins."

The terms "HMG-CoA reductase inhibitor(s)" and "statin(s)" are used interchangeably herein and, unless otherwise noted, are intended to include all lactone and open-ring 3,5-dihydroxy open-acid forms of HMG-CoA reductase inhibitors and the pharmaceutically acceptable salts and esters thereof; and therefor the use of such lactone and open-ring 3,5-dihydroxy acid forms and salts and esters thereof are included within the scope of this invention. The term "open acid statin" as used herein specifically refers to the 3,5-dihydroxy open-acid form of a statin. The terms "lovastatin acid" (or LVA) and "simvastatin acid" (or SVA) used herein refer to the open acid form of these statins.

Examples of HMG-CoA reductase inhibitors that may be used within the scope of the present invention include but are not limited to the lactonized and dihydroxy open acid forms and pharmaceutically acceptable salts and esters thereof of: lovastatin (MEVACOR®, see U.S. Pat. No. 4,342,767); simvastatin (ZOCOR®; see U.S. Pat. No. 4,444,784); pravastatin, particularly the sodium salt thereof (PRAVACHOL®; see U.S. Pat. No. 4,346,227); fluvastatin particularly the sodium salt thereof (LESCOL®; see U.S. Pat. No. 5,354,772); atorvastatin, particularly the calcium salt thereof (LIPITOR®; see U.S. Pat. No. 5,273,995); pitavastatin also referred to as NK-104 (see PCT international publication number WO 97/23200); and rosuvastatin also known as ZD4522 (CRESTOR®; see U.S. Pat. No. 5,260,440, and Drugs of the Future, 1999, 24(5), pp. 511-513). Due to its worldwide withdrawal, cerivastatin can be used within the scope of this invention for screening, testing and the like, but is necessarily restricted only to approved uses with regard to administration to humans. The structural formulas of several of these statins and additional HMG-CoA reductase inhibitors are described at page 87 of M. Yalpani, "Cholesterol Lowering Drugs", Chemistry & Industry, pp. 85-89 (5 Feb. 1996). Descriptions of the marketed statins are also found in the current edition of the Physicians Desk Reference. Furthermore, compounds other than those noted above which are determined to be HMG-CoA reductase inhibitors can be employed in the screening methods and other methods of this invention. Particularly, the HMG-CoA reductase inhibitor is selected from lovastatin and simvastatin, which are lactonized statins, and their corresponding dihydroxy open acid forms and the pharmaceutically acceptable salts thereof. More particularly, the HMG-CoA reductase inhibitor is selected from simvastatin, open-acid simvastatin and the pharmaceutically acceptable salts thereof.

Compounds that are inhibitors of CYP3A4 can be identified using the in vitro assay of midazolam 1'-hydroxylation described in Backman, et al., Plasma concentrations of active simvastatin acid are increased by gemfibrozil, Clin. Pharmacology & Therapeutics, vol 68:2, 122-129 (August 2000), herein incorporated by reference.

Herein, the term "pharmaceutically acceptable salts" shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenzimidazole, diethylamine, piperazine, morpholine, 2,4,4-trimethyl-2-pentamine and tris(hydroxymethyl)aminomethane. Pharmaceutically acceptable esters at the carboxylic acid group can be made by treating a dihydroxy open acid statin with an alcohol. Examples of pharmaceutically acceptable esters of dihydroxy open acid statins include, but are not limited to, —$C_{1-4}$ alkyl and —$C_{1-4}$ alkyl substituted with phenyl-, dimethylamino-, and acetylamino. "$C_{1-4}$ alkyl" herein includes straight or branched aliphatic chains containing from 1 to 4 carbon atoms, for example methyl, ethyl, n-propyl, n-butyl, iso-propyl, sec-butyl and tert-butyl.

The term "therapeutically effective amount" is intended to mean that amount of a drug or pharmaceutical agent that will elicit the biological or medical response of a tissue, a system, animal or human that is being sought by a researcher, veterinarian, medical doctor or other clinician. Particularly with respect to statins, the dosage a patient receives can be selected so as to achieve the amount of LDL (low density lipoprotein) cholesterol lowering desired; the dosage a patient receives may also be titrated over time in order to reach a target LDL level. The dosage regimen utilizing a statin or a drug combination comprised of a statin and a non-statin is selected in accordance with a variety of factors including type, species, age, weight, sex and medical condition of the patient; the severity of the condition to be treated; the potency of the compound chosen to be administered; the route of administration; and the renal and hepatic function of the patient. A consideration of these factors is well within the purview of the ordinarily skilled clinician for the purpose of determining a therapeutically effective or prophylactically effective dosage amount needed to prevent, counter, or arrest the progress of the condition.

The term "patient" as used herein includes mammals, especially humans. Administering of the drug to the patient includes both self-administration and administration to the patient by another person. The patient may be in need of treatment for an existing disease or medical condition, or may desire prophylactic treatment.

The oral dosage amount of the statin is from about 1 to 200 mg/day, and more preferably from about 5 to about 40 mg/day. However, daily dosage amounts will vary depending on factors as noted above, including the potency of the particular compound, and may be in sub-milligram amounts. Although the statin may be administered in divided doses, for example from one to four times daily, a single daily dose of the drug is preferred. As examples, the daily dosage amount may be selected from, but not limited to 5 mg, 10 mg, 15 mg, 20 mg, 25 mg, 40 mg, 50 mg, 75 mg, 80 mg, 100 mg, 150 mg, 160 mg and 200 mg.

The term "non-statin" as used herein is intended to mean any pharmaceutically active drug other than an HMG-CoA reductase inhibitor. Non-statin drugs are often co-administered with a statin to patients who need a variety of therapeutic treatments.

"Co-administration" as intended herein, includes administration of a single pharmaceutical dosage formulation which contains both a statin and a non-statin drug, as well as administration of each drug in its own separate pharmaceutical dosage formulation. Where separate dosage formulations are used, the statin and the non-statin drug can be administered at essentially the same time, i.e., concurrently, or at separately staggered times, i.e., sequentially, and the instant invention encompasses all these regimens.

Non-statin drugs are pharmaceutical drugs that could potentially be co-administered with a statin to a patient include lipid modifying agents that are not inhibitors of HMG-CoA reductase inhibitors, drugs that have other non-lipid related pharmaceutical activities, or drugs that have both lipid-lowering effects and other pharmaceutical activities. Examples of additional active agents which may be employed include but are not limited to HMG-CoA synthase inhibitors; squalene epoxidase inhibitors; squalene synthetase inhibitors (also known as squalene synthase inhibitors), acyl-coenzyme A: cholesterol acyltransferase (ACAT) inhibitors including selective inhibitors of ACAT-1 or ACAT-2 as well as dual inhibitors of ACAT-1 and -2; microsomal triglyceride transfer protein (MTP) inhibitors; probucol; niacin; cholesterol absorption inhibitors such as ezetimibe (also known as SCH-58235), which is described in U.S. Pat. Nos. 5,767,115 and 5,846,966; bile acid sequestrants; LDL (low density lipoprotein) receptor inducers; platelet aggregation inhibitors, for example glycoprotein IIb/IIIa fibrinogen receptor antagonists and aspirin; human peroxisome proliferator activated receptor gamma (PPARγ) agonists including the compounds commonly referred to as glitazones for example, pioglitazone and rosiglitazone and, including those compounds included within the structural class known as thiazolidinediones as well as those PPARγ agonists outside the thiazolidinedione structural class; PPARα agonists such as derivatives of fibric acid including bezafibrate, clofibrate, fenofibrate including micronized fenofibrate, and gemfibrozil; PPAR dual α/γ agonists; PPARδ agonists, vitamin $B_6$ (also known as pyridoxine) and the pharmaceutically acceptable salts thereof such as the HCl salt; vitamin $B_{12}$ (also known as cyanocobalamin); folic acid or a pharmaceutically acceptable salt or ester thereof such as the sodium salt and the methylglucamine salt; antioxidant vitamins such as vitamin C and E and beta carotene; beta-blockers; angiotensin II antagonists such as losartan; angiotensin converting enzyme inhibitors such as enalapril and captopril; calcium channel blockers such as nifedipine and diltiazam; endothelian antagonists; agents that enhance ABC1 gene expression; FXR and LXR ligands including both inhibitors and agonists; bisphosphonate compounds such as alendronate sodium; and cyclooxygenase-2 inhibitors such as rofecoxib and celecoxib.

Particularly, the non-statin pharmaceutical drugs for use in the practice of this invention are any of the PPAR receptor agonists, including those that are selective for one PPAR receptor sub-type as well as those that are active for two or more receptor sub-types. More particularly, the non-statin pharmaceutical drugs are PPARα agonists such as the fibric acid derivatives; PPARγ agonists; and dual PPARα/γ agonists, i.e., those having dual activity for both the α and the γ receptor sub-types.

When a statin and a non-statin are referred to as competitively binding to an enzyme or enzyme isoform (i.e., isozyme), it means both the statin and the non-statin bind to the same enzyme or isozyme. An adverse pharmacokinetic drug interaction is intended to mean an in vivo interaction between a statin and a co-administered non-statin pharmaceutical drug in a mammal, particularly a human, which raises the plasma level of active open-acid statin above the level it would be at if the statin was administered alone, i.e., absent the co-administered non-statin.

EXAMPLE 1

Studies on Glucuronidation of Statins

The term "glucuronidation assay" as used herein refers to the following assay when performed with human liver microsomes.

A typical incubation mixture, in a final volume of 0.3 ml, contained 0.45 mg liver microsomes, preincubated with 0.045 mg Brij 58 for (or 0.0225 mg alamethicin) 15 min, 20 mM $MgCl_2$, 5 mM UDPGA, and 0.05 M Tris buffer, pH 7.0. Kinetic studies were conducted using 0.2-200 μM statins in liver microsomal preparations from humans or animals. Unless otherwise specified, the reaction was started by the addition of statins following a 3-min pre-incubation at 37° C., and the reaction was incubated for 45-60 min. Control experiments included incubation mixtures with either microsomes or UDPGA missing. The reaction was terminated, at appropriate time intervals, by the addition of 0.8 ml acetonitrile (ACN). The ACN extracts were evaporated to dryness and reconstituted for analysis by a high-performance liquid chromatography (HPLC) method, with UV and/or MS detection.

The ability of statins to undergo glucuronidation was measured by formation of statin glucuronide and statin lactones, and expressed in term of intrinsic clearance (Clint). The CLint was estimated by dividing Vmax by apparent Km. The Km and Vmax values were estimated using a nonlinear regression program, based on a Micheallis-Menten equation as follow:

$V=Vmax \times C/(Km+C)$; $V$=formation rate of statin glucuronide+lactone, and C=substrate concentration.

EXAMPLE 2

The term "UGT-specific glucuronidation assay" as used herein refers to the following assay as performed with specific human recombinant UGT isoforms (isozymes).

To examine UGT isoforms responsible for the glucuronidation of statins, incubations with various human recombinant UGT isoforms were performed using the same conditions as described herein for human liver microsomes in Example 1, except that the mixture contained 0.3 mg UGTs and was incubated for up to 60 min. Control incubations using microsomes isolated from the same cell line, containing the vector but without a cDNA insert, also were included.

EXAMPLE 3

Studies to Evaluate Susceptibility of Statins to Inhibition by Various Inhibitors of Glucuronidation The term "glucuronidation inhibition assay" as used herein refers to the following assay when performed with human liver microsomes.

A typical incubation mixture, in a final volume of 0.3 ml, contained 0.45 mg human or animal liver microsomes, pre-incubated with 0.045 mg Brij 58 (or 0.0225 mg alamethicin) for 15 min, 20 mM $MgCl_2$, 5 mM UDPGA, and 0.05 M Tris buffer, pH 7.0. Inhibitors (prepared in 50% acetonitrile water at various concentrations, and used 5 μl for specified final concentrations) or 50% acetonitrile in water (5 μl, control) was co-incubated with the substrates (open-acid statins prepared in 50% acetonitrile in water and used 5 μl for a 10-20 μM final concentration (or at concentration which is below or comparable to the respective Km value for each statin). Incubations were conducted at 37° C. and were terminated after 45-60 min, by the addition of 0.8 ml acetonitrile. The acetonitrile extracts were evaporated to dryness and reconstituted for analysis by a high-performance liquid chromatography method with UV and/or MS detection.

The effects of inhibitors on metabolism of the statins were expressed as percentages of metabolites (statin glucuronides and lactones) formed in the presence of inhibitors relative to the corresponding values obtained in the absence of inhibitors (control) on the same day. The concentration of inhibitors producing a 50% decrease in the metabolism of statins (IC50) was determined using non-linear regression analysis, based on the following relationship:

$$E = Emax \cdot [1-(C/C+IC50)]$$

EXAMPLE 4

As was observed in humans, gemfibrozil increased the AUC and Cmax of SVA, but not of SV, in dogs dosed with SV. Therefore, dog was determined to be an appropriate animal model for studies on the SV-gemfibrozil PK interaction. See Table 1.

EXAMPLE 5

Figure 2:
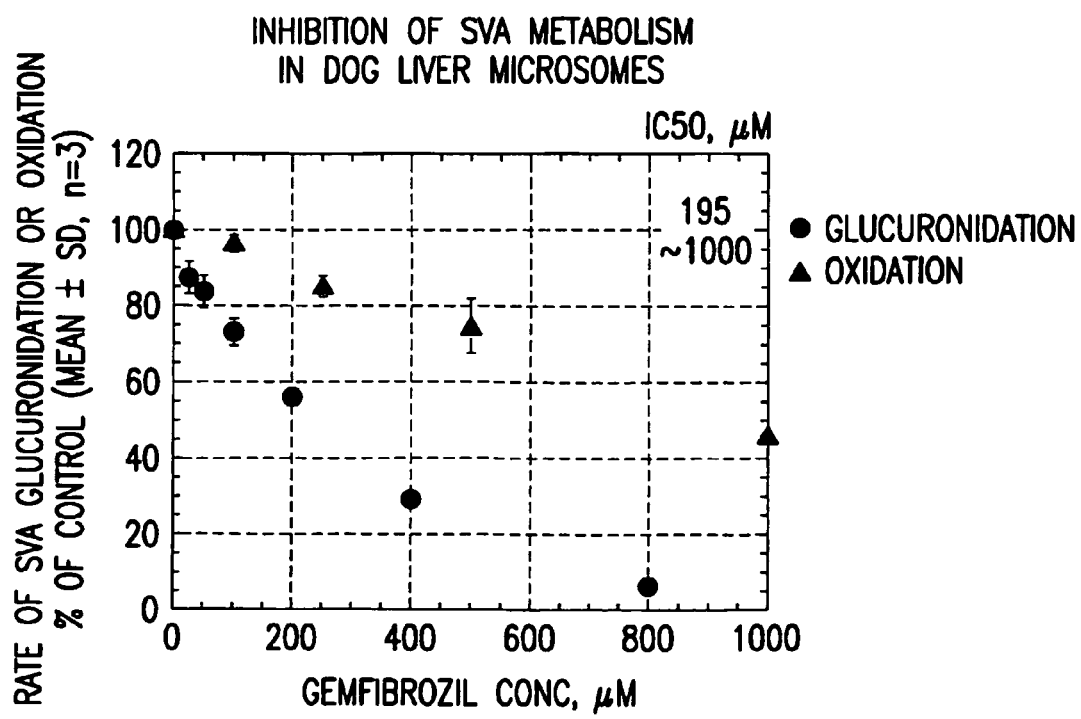
FIG. 2 shows inhibition of simvastatin acid glucuronidation and oxidation by gemfibrozil in dog liver microsomes.
Figure 3:
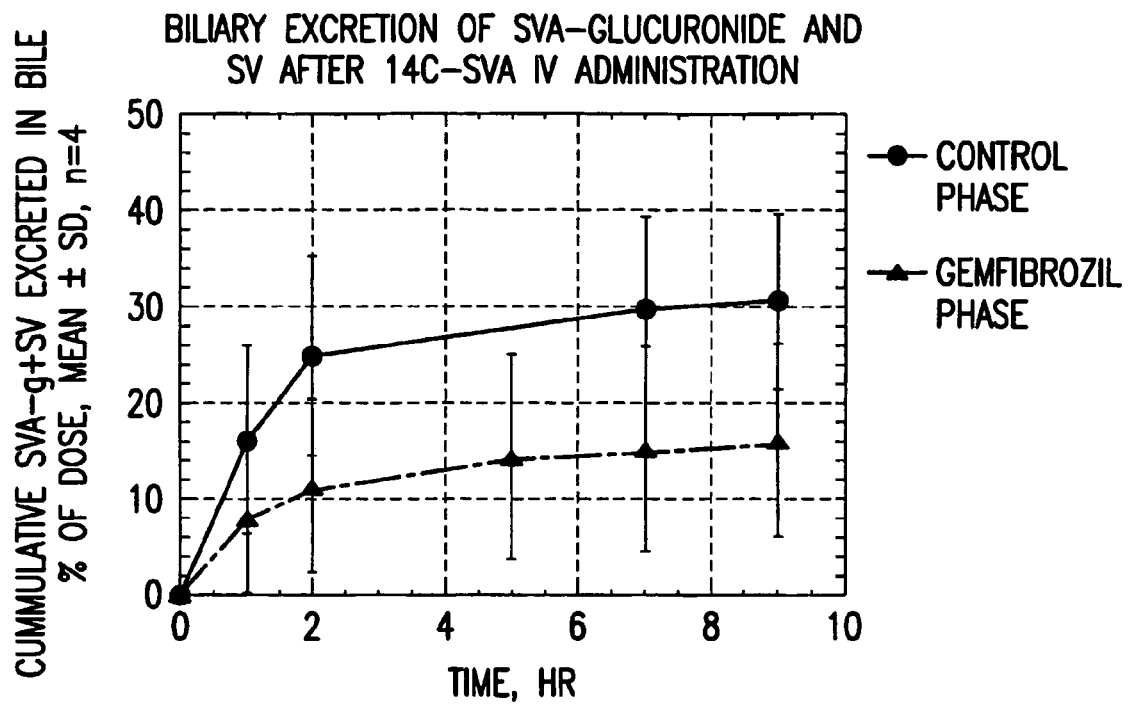
FIG. 3 shows biliary excretion of simvastatin acid-glucuronide and simvastatin in vivo in dogs.

In Dogs, Gemfibrozil Caused:
  Minimal effect on ex vivo simvastatin hydrolysis. See FIG. 1.
  Marked inhibition of SVA glucuronidation in vitro, in contrast to SVA oxidation. See FIG. 2.
  Significant decrease in clearance of SVA and biliary excretion of SVA-glucuronide in vivo. See FIG. 3.

Conclusion: In dogs, gemfibrozil-mediated elevations of SVA AUC following SV administration are due, at least in part, to the inhibitory activity of gemfibrozil on SVA glucuronidation.

EXAMPLE 6

Figure 4:
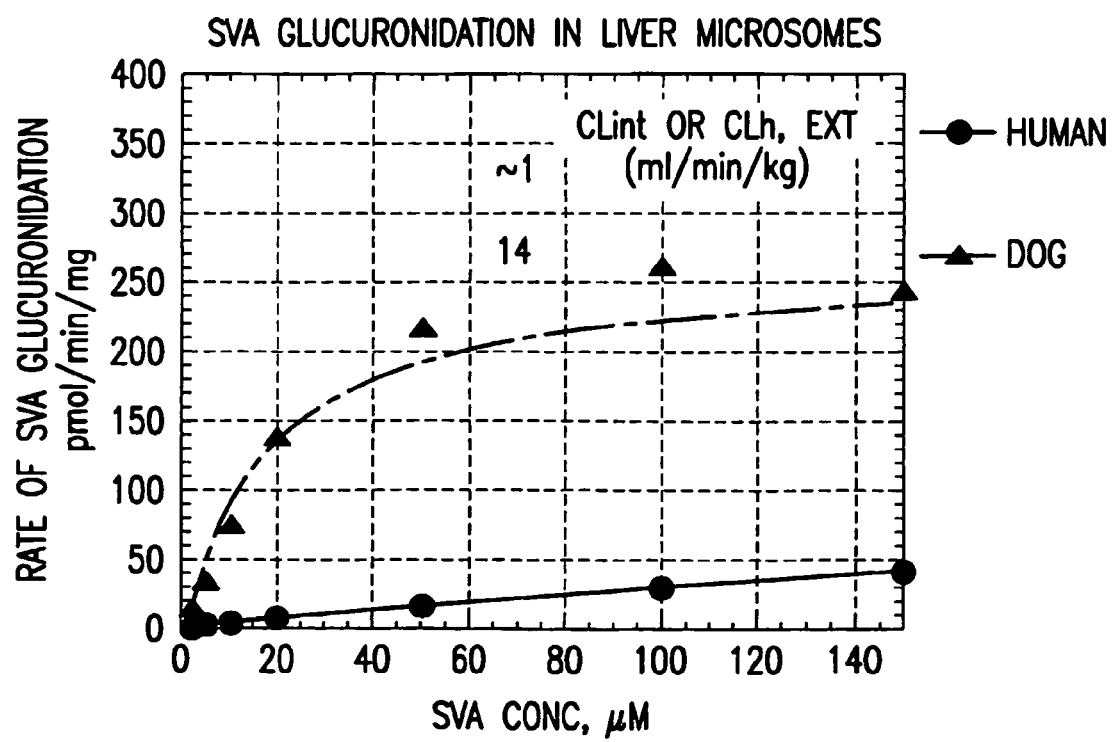
FIG. 4 shows simvastatin acid (SVA) glucuronidation in human liver microsomes.
Figure 5:
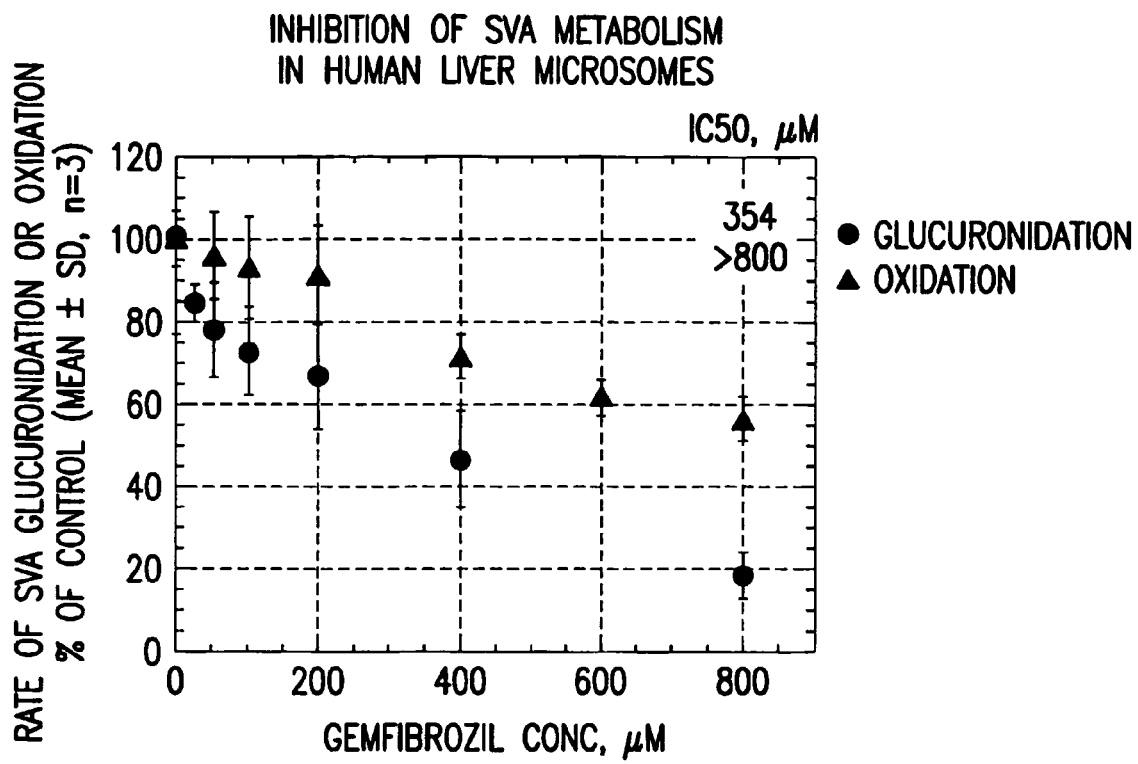
FIG. 5 shows in vitro rate of inhibition of SVA metabolism (glucuronidation and oxidation) by gemfibrozil in human liver microsomes.
Figure 6:
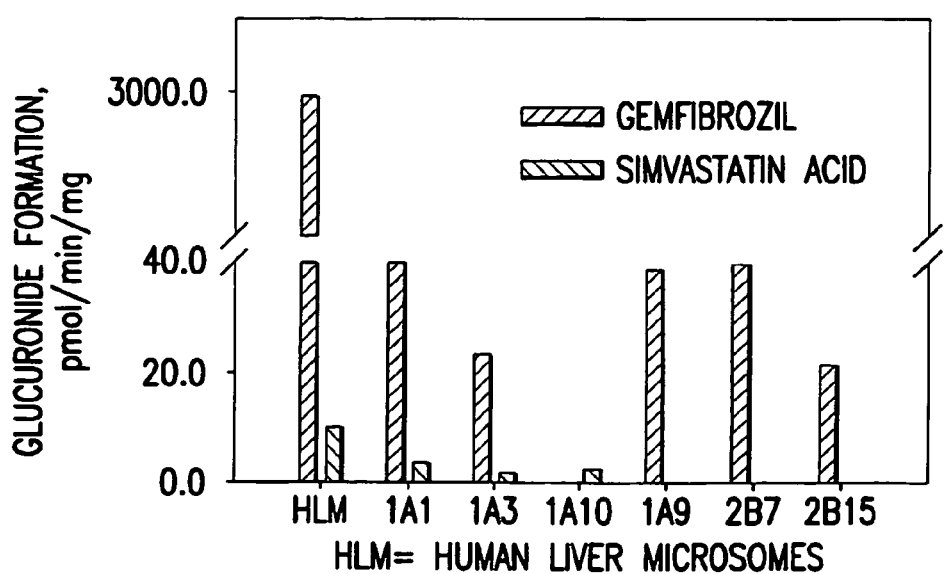
FIG. 6 shows the rate of glucuronide formation of gemfibrozil and SVA by various UGT isozymes.

In Humans:
  Glucuronidation of SVA was observed in vitro and in vivo, but to a lesser extent than was the case in dogs. See FIG. 4.
  In vitro, gemfibrozil caused more pronounced inhibition of the glucuronidation of SVA than CYP3A-mediated oxidative pathways, similar to the case in dogs. See FIG. 5.
  Glucuronidation of gemfibrozil and SVA is catalyzed by at least two common human UGT isozymes (UGT1A1 and 1A3, See FIG. 6)—competitive inhibition was demonstrated in vitro. Glucuronidation of SVA is also catalyzed by UGT1A10.

Conclusion: In humans, gemfibrozil-mediated elevations of SVA AUC following SV administration are due, at least in part, to the inhibitory activity of gemfibrozil on SVA glucuronidation.

EXAMPLE 7

In Vitro Glucuronidation of Statins

In Human Liver Microsomes:
  Cerivastatin (CVA) and atorvastatin (AVA) formed an acyl glucuronide conjugate. See Table 2.

TABLE 1

Pharmacokinetics of simvastatin and simvastatin acid after simvastatin administration (4 mg/kg po) to dogs (n = 5) pretreated with vehicle or gemfibrozil (75 mg/kg, bid) for 5 days

| Compound measured | Vehicle phase | | Gemfibrozil phase | | Ratio (Range) Gemfibrozil/Vehicle | |
|---|---|---|---|---|---|---|
| | AUC 24 hr ng/ml · hr | Cmax ng/ml | AUC 24 hr ng/ml · hr | Cmax ng/ml | AUC | Cmax |
| Simvastatin | 154.4 ± 65 | 47.5 ± 26 | 76.6 ± 18* | 11.3 ± 3.9** | 0.6 ± 0.3 (0.2-1.0) | 0.3 ± 0.2 (0.1-0.5) |
| Simvastatin acid | 120.4 ± 72 | 43.8 ± 26 | 295. ± 109* | 80.8 ± 17* | 3.5 ± 2.9 (0.9-8.5) | 2.6 ± 2.0 (0.9-5.9) |
| | | | AUC 12 hr uM · hr | Cmax uM | | |
| Gemfibrozil | — | — | 1441 ± 176 | 446 ± 66 (330-500) | | |

*p < 0.10
**p < 0.05

The relative contribution of the glucuronidation pathway to overall metabolism was considerably higher for CVA than for AVA or SVA. See Table 2.

Figure 7:
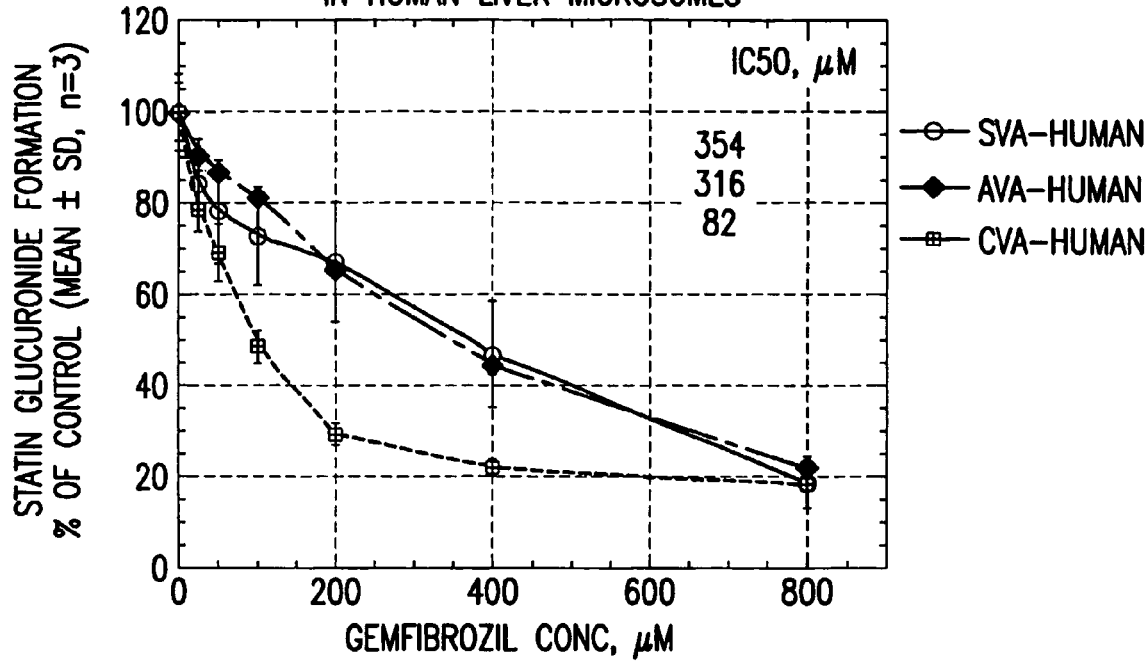
FIG. 7 shows the inhibitory effect of gemfibrozil on in vitro formation of SVA-glucuronide, atorvastatin-glucuronide and cerivastatin-glucuronide in human liver microsomes.

CVA glucuronidation was more susceptible to inhibition by gemfibrozil than was SVA or AVA glucuronidation. See FIG. 7.

Glucuronidation of these statins is mediated by at least two common human UGT isozymes (UGT1A1 and 1A3).

TABLE 2

Metabolism of statins in human liver microsomes: Preliminary data

| | CLint (ul/min/mg protein) | | |
|---|---|---|---|
| Statin | Oxidation* | Glucuronidation | Relative Contribution |
| SVA | 50 | 0.4 | 1 |
| AVA | 50 | 4.0 | 7 |
| CVA | 10** | 2.9 | 22 |

*mediated primarily by CYP3A (SVA and AVA) or CYP3A and CYP2C8 (CVA).
**based on 2-point determination.

EXAMPLE 8

Gemfibrozil Versus Fenofibrate

In dog liver microsomes, gemfibrozil was more potent than fenofibrate as an inhibitor of SVA glucuronidation. See Table 3.

Consistent with the in vitro data, the effect of gemfibrozil on SVA PK in dogs after oral administration of SV was greater than that of fenofibrate, and appeared to occur via a different mechanism. See Table 3.

TABLE 3

| | | In vivo (Dogs) | |
|---|---|---|---|
| Compound measured | In vitro dog liver microsomes | Gemfibrozil treated AUC ratio Gem/vehicle | Fenofibrate treated AUC ratio Feno/vehicle |
| Simvastatin (SV) | | 0.6 ± 0.3 (0.2-1.0) | 2.2 ± 0.7 (1.5-3.3) |
| Simvastatin acid (SVA) | | 3.5 ± 2.9 (0.9-8.5) | 1.7 ± 0.2 (1.4-2.0) |
| SVA/SV | | 5.4 ± 2.1 (3.3-8.7) | 0.8 ± 0.2 (0.6-1.0) |

| | IC50* uM | Cmax uM | Cmax uM |
|---|---|---|---|
| Gemfibrozil | 195 | 446 ± 66 (330-500) | — |
| Fenofibric acid | 283 | — | 77 ± 9.7 (63-87) |

*IC50 values for gemfibrozil or fenofibric acid as inhibitors of SVA glucuronidation in dog liver microsomes

EXAMPLE 9

Gemfibrozil versus Fenofibrate: In Vitro Studies

In human liver microsomes, gemfibrozil is more potent than fenofibrate as an inhibitor of statin glucuronidation. See table 4.

In humans, exposure to gemfibrozil is greater than exposure to fenofibrate/fenofibric acid at their respective therapeutic doses.

Figure 8:
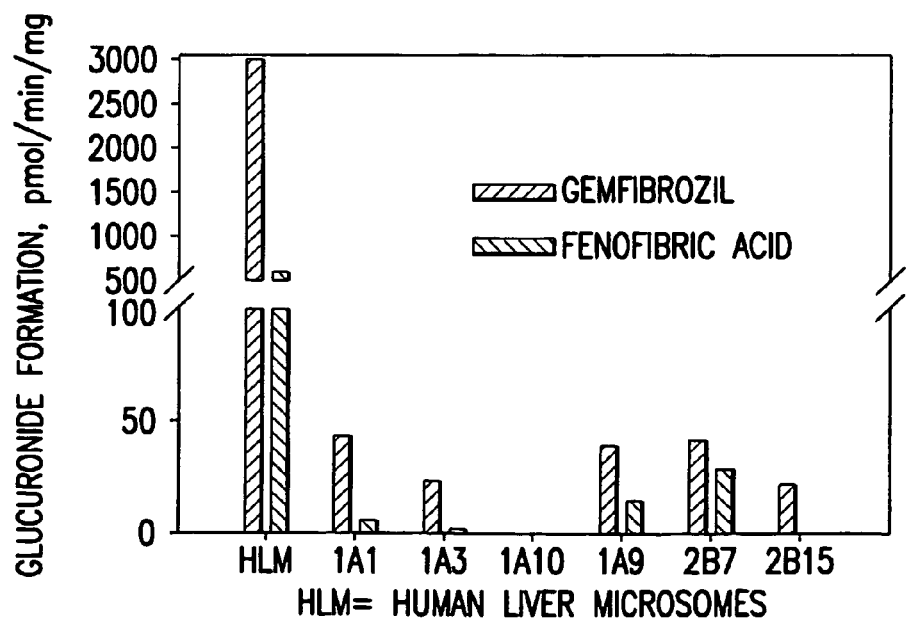
FIG. 8 shows the rate of glucuronide formation of gemfibrozil and fenofibric acid by various UGT isozymes.

Unlike the situation with gemfibrozil, the glucuronidation of fenofibrate appeared to be catalyzed primarily by UGT1A9 and isoforms of the UGT2B subfamily. See FIG. 8.

TABLE 4

Fibrates as inhibitors of glucuronidation

| | IC50*, uM | | | Cmax** |
|---|---|---|---|---|
| | SVA-G | AVA-G | CVA-G | uM |
| Gemfibrozil | 354 | 316 | 82 | 100-300 |
| Fenofibrate*** | 682 | not done | 433 | 15-55 |

*obtained following co-incubation of fibrates and SVA in human liver microsomes.
**reported values following 600 mg bid gemfibrozil or 200 mg qd fenofibrate in humans.
***measured as fenofibric acid.

EXAMPLE 10

The rate of glucuronide formation for simvastatin (SVA), atorvastatin (AVA), cerivastatin (CVA) and rosuvastatin (RVA) by UGT isoforms in liver microsomes is shown in Table 5.

TABLE 5

| | Rate of Glucuronide Formation, pmol/min/mg | | |
|---|---|---|---|
| Substrate | Human Liver Microsomes | UGT1A1 | UGT1A3 |
| SVA | 32 ± 20 | 5 ± 2 | 2 ± 1 |
| AVA | 53 ± 26 | 8 ± 1 | 2 ± 1 |
| CVA | 67 ± 3 | 7 ± 3 | 2 ± 1 |
| RVA | 55 ± 3 | 20 ± 4 | 5 ± 2 |

Incubations were performed in triplicate for human liver microsomes (pooled from n=10) or UGTs at 250-μM substrate concentration. Values are mean±SD (n=3 to 5).

EXAMPLE 11

In Vitro Oxidative Metabolism Studies

The term "oxidation inhibition assay" as used herein refers to the following assay when performed with human liver microsomal protein.

For oxidative metabolism studies, a typical incubation mixture, in a final volume of 0.5 mL, contained 0.1-0.25 mg liver microsomal protein, 0.1M sodium phosphate buffer (pH 7.4), 10 mM $MgCl_2$, and 1 mM NADPH. Gemfibrozil (GFZ) (prepared in 50% acetonitrile in water at various concentrations) or 50% acetonitrile in water (control) was co-incubated with the substrates (statins prepared in 50% acetonitrile in water for a 10-20-μM final concentration, which was below or comparable to the respective $K_m$ value for each statin). Incubations were conducted at 37° C. and were terminated after 10-20 min (with NADPH) by the addition of ACN (acetonitrile). The ACN extracts were evaporated to dryness and reconstituted for analysis by HPLC with UV detection.

Analytical Procedures for Statins and Oxidative Metabolites

Quantitation of levels of SVA, CVA, and AVA and their oxidative metabolites from in vitro incubations was performed using HPLC methods as previously described in Prueksaritanont, T., Ma, B., Tang, Meng, Y., Assang, C., Lu, P., Reider, P. J., Lin J. H., and Baillie, T. A.: Metabolic interactions between mibefradil and HMG-CoA reductase inhibitors: an in vitro investigation with human liver preparations. Br. J. Clin. Pharmacol., 47: 291-298 (1999), herein incorporated by reference. In brief, samples, held in an autosampler set at 5° C., were chromatographed on either a Betasil $C_{18}$ (250×4.6 mm, 5 μm) or a Zorbax $C_{18}$ (Waters, 150×4.6 mm, 5 μm) column, preceded by a $C_{18}$ guard column, with a linear gradient of acetonitrile in 10 or 25 mM ammonium acetate, pH 4.5. The eluate was monitored by UV absorption set at γ=240 nm (SVA, and AVA) or γ=272 nm (CVA), and/or by an on-line IN/US β-RAM radioactivity detector (IN/US Systems, Tampa, Fla.). Due to unavailability of authentic standards for oxidative metabolites of statins, quantitation of these metabolites in the in vitro incubation mixtures was accomplished using standard curves for their respective statins, assuming identical extraction recoveries and extinction coefficients between the parent drug and its corresponding metabolites.

Identification of statin metabolites was accomplished by using LC-MS/MS techniques (BP-1050 gradient system, Hewlett Packard, San Fernando, Calif.; Finnigan MAT LCQ ion trap mass spectrometer, Finnigan-MAT, San Jose, Calif.). Mass spectral analyses were performed using electrospray ionization (ESI) in the negative ion mode (for statin glucuronide conjugates and oxidative metabolites) or positive ion mode (for statin lactones). The ESI voltage was set at 4 kV, with the heated capillary temperature held at 230° C.

EXAMPLE 12

Figure 9A:
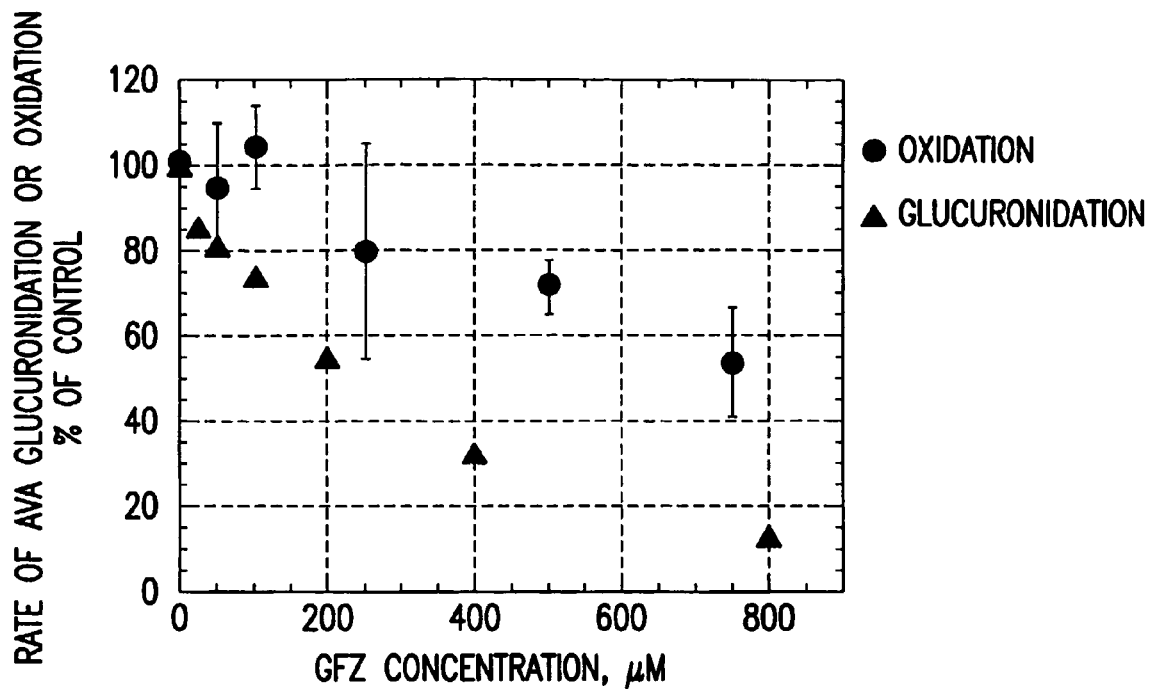
FIG. 9 shows the effect of gemfibrozil (GFZ) on the glucuronidation and oxidation of atorvastatin (AVA) (FIG. 9A) and cerivastatin (CVA) (FIG. 9B) in human liver microsomes.
Figure 9B:
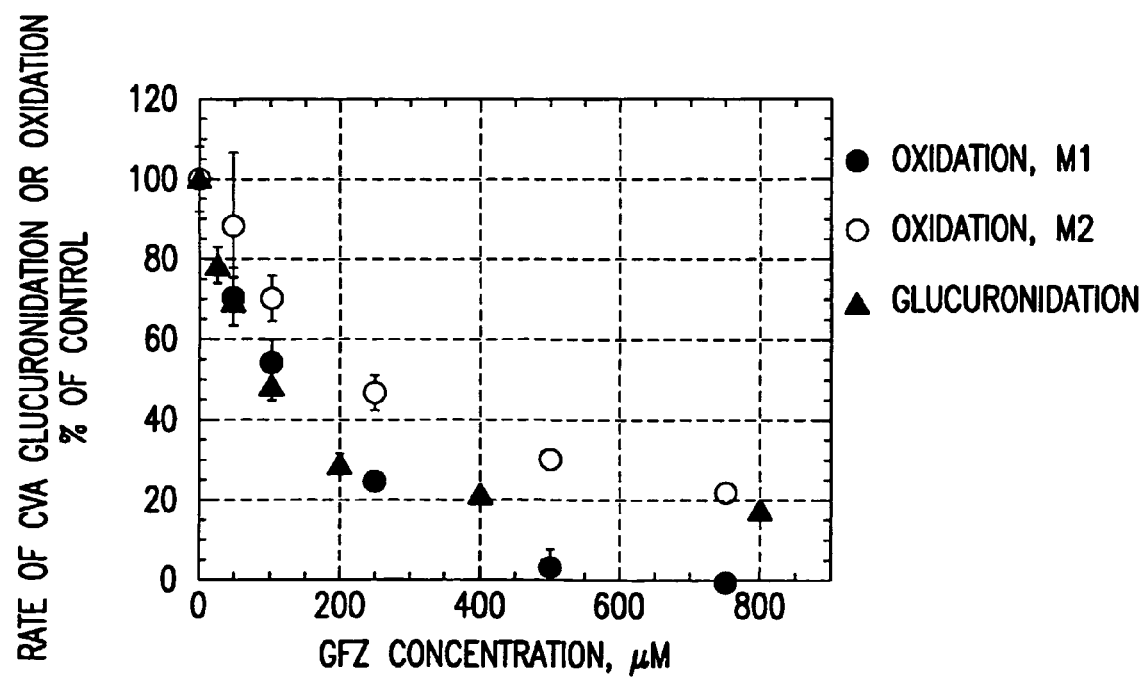

In the case of AVA and CVA, two major metabolites of each statin were observed in liver microsomes supplemented with NADPH. Based on previous reports (Boberg et al., Drug Metab Dispos. 1997 March, 25(3):321-31; and Prueksaritanont et al., Br. J. Clin. Pharmacol., 47: 291-298 (1999), ibid.), these metabolites are believed to be two hydroxylated products of AVA, and hydroxylated (M1) and O-demethylated (M2) metabolites of CVA. As was noted with SVA, formation of the two oxidative metabolites of AVA was less susceptible to inhibition by GFZ than was the glucuronide conjugate of this statin (FIG. 9A); the $IC_{50}$ values were >750 and 314 μM for the oxidation and glucuronidation reactions, respectively (Table 6). In contrast, the formation of both CVA oxidative and glucuronide metabolites of CVA was markedly inhibited by GFZ (FIG. 9B). In fact, the inhibitory potency of GFZ on oxidative metabolite M1 ($IC_{50}$=87 μM) was comparable to that on the generation of CVA glucuronide formation ($IC_{50}$=82 μM) (Table 6). These $IC_{50}$ values for the glucuronidation and oxidation (both M1 and M2) of CVA were much lower than those for the corresponding metabolic pathways of SVA and AVA (Table 6). Under the present in vitro incubation conditions, both oxidative metabolites of AVA were markedly inhibited (>90%) by the potent CYP3A inhibitor ketoconazole (1 μM). In contrast, ketoconazole, at 1 μM, inhibited the formation of the oxidative metabolites of CVA by less than or approximately 50% (Table 6).

The inhibitory effects of gemfibrozil (GFZ) ($IC_{50}$, μM) and ketoconazole (percent inhibition at 1-μM concentration) on the glucuronidation and oxidation of simvastatin (SVA), atorvastatin (AVA), cerivastatin (CVA) and rosuvastatin (RVA) in human liver microsomes are shown in Table 6.

TABLE 6

|  |  | Gemfibrozil $IC_{50}$, μM | Ketoconazole % Inhibition |
|---|---|---|---|
| SVA | Glucuronidation | 354 | — |
|  | Oxidation | >800 | >85 |
| AVA | Glucuronidation | 316 | — |
|  | Oxidation | >750 | >90 |
| CVA | Glucuronidation | 82 | — |
|  | Oxidation (M1) | 87 | 68 |
|  | Oxidation (M2) | 220 | ~50 |
| RVA | Glucuronidation | ~400 | — |

Incubations were performed in triplicate for each concentration of inhibitors, and involved co-incubation of GFZ or ketoconazole (1 μM) with statins (10-20 μM) in the presence of NADPH (oxidation) or UDPGA (glucuronidation).

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the active agents used in the instant invention as indicated above. Likewise, the specific pharmacological responses observed may vary according to and depending upon the particular active compound selected or whether there are present pharmaceutical carriers, as well as the type of formulation employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A method for appropriately selecting a statin and a non-statin drug for co-administration to a patient in need of such co-administered drug treatment to avoid or minimize an increase in the plasma levels of the open-acid form of the statin, wherein the open-acid form of the statin is susceptible to human metabolic glucuronidation to form an acyl glucuronide conjugate by a human uridine 5'-diphosphate-glucuronosyltransferase (UGT) isozyme, comprising:
   (a) testing the statin in a human UGT-specific glucuronidation assay to identify which one or more UGT isozymes are responsible for glucuronidation of the open-acid form of the statin to form an acyl glucuronide conjugate, and
   (b) selecting the non-statin as appropriate for co-administration with the statin if:
      (i) the non-statin is not metabolically glucuronidated as determined by testing the non-statin in a glucuronidation assay, or
      (ii) the non-statin is not metabolically glucuronidated by any of the one or more UGT isozymes identified in step (a) as determined by testing the non-statin in the UGT-specific glucuronidation assay.

2. The method of claim 1, wherein the statin is selected from lovastatin, simvastatin, fluvastatin, atorvastatin, pitavastatin and rosuvastatin in their lactonized and dihydroxy open acid forms and the pharmaceutically acceptable salts thereof.

3. A method for appropriately selecting a statin and a non-statin drug for co-administration to a patient in need of such co-administered drug treatment to avoid or minimize an increase in the plasma levels of the open-acid form of the statin, wherein the open-acid form of the statin is susceptible to human metabolic glucuronidation to form an acyl glucuronide conjugate by a human UGT isozyme, comprising:

(a) testing the statin in a human UGT-specific glucuronidation assay to identify which one or more UGT isozymes are responsible for glucuronidation of the open-acid form of the statin to form an acyl glucuronide conjugate, and (b) selecting the non-statin as appropriate for co-administration with the statin if:
   (i) the non-statin is not metabolically glucuronidated as determined by testing the non-statin in a human glucuronidation assay, or
   (ii) the non-statin is not metabolically glucuronidated by any of the one or more UGT isozymes identified in step a) as determined by testing the non-statin in the UGT-specific glucuronidation assay; wherein the non-statin is an agonist of at least one receptor selected from the group consisting of PPARα, PPARδ and PPARγ, and the statin is selected from lovastatin, simvastatin, fluvastatin, atorvastatin, pitavastatin and rosuvastatin in their lactonized and dihydroxy open acid forms and the pharmaceutically acceptable salts thereof.

4. The method of claim 3, wherein the non-statin is selected from the group consisting of a PPARα agonist, a PPARδ agonist and a dual PPARα/γ agonist.

5. A method for appropriately selecting a statin and a non-statin drug that do not bind to one or more of the same human UGT isozymes for co-administration to a patient in need of such co-administered drug treatment to avoid or minimize an increase in the plasma levels of the open-acid form of the statin, wherein the open-acid form of the statin is susceptible to human metabolic glucuronidation by at least one UGT isozyme to form an acyl glucumnide conjugate, comprising:

(a) testing the non-statin in a glucuronidation inhibition assay to determine if the non-statin inhibits the metabolic glucuronidation of the statin; and (b) selecting the non-statin drug as appropriate for co-administration if it does not inhibit the metabolic glucuronidation of the statin.

6. The method of claim 5, wherein the statin and the non-statin additionally do not competitively bind to an isozyme selected from the group consisting of CYP3A4, CYP2C8 and CYP2C9.

7. The method of claim 5, wherein the statin and the non-statin drug do not competitively bind to one or more of the same human UGT isozymes, and in step (a), the non-statin is tested to determine if it competitively inhibits the metabolic glucuronidation of the statin.

8. The method of claim 5, wherein the statin is selected from lovastatin, simvastatin, fluvastatin, atorvastatin, pitavastatin and rosuvastatin in their lactonized and dihydroxy open acid forms and the pharmaceutically acceptable salts thereof.

9. The method of claim 6, wherein the statin is selected from lovastatin, simvastatin, fluvastatin, atorvastatin, pitavastatin and rosuvastatin in their lactonized and dihydroxy open acid forms and the pharmaceutically acceptable salts thereof.

10. The method of claim 7, wherein the statin is selected from lovastatin, simvastatin, fluvastatin, atorvastatin, pitavastatin and rosuvastatin in their lactonized and dihydroxy open acid forms and the pharmaceutically acceptable salts thereof.

11. A method for screening a statin to determine if it is potentially susceptible to an adverse pharmacokinetic drug interaction that could increase the plasma levels of open-acid statin in a patient who is a co-administered a non-statin drug that is metabolically glucuronidated in a human comprising:

(a) testing the statin in a human glucuronidation assay to determine if the open-acid form of the statin is metabolically glucuronidated to form an acyl glucuronide conjugate, and if so (b) testing the non-statin to determine the concentration which reduces enzyme activity by 50% ($IC_{50}$) of the non-statin relative to the statin in the glucuronidation inhibition assay; and (c) determining that the statin is not susceptible to an adverse pharmacokinetic drug interaction with the non-statin if the non-statin drug has an $IC_{50}$ value relative to the statin in the glucuronidation inhibition assay that is 5-fold or more greater than the maximum plasma concentration obtained following a daily therapeutic dose of the non-statin drug.

12. The method of claim 11, wherein the statin is selected from lovastatin, simvastatin, fluvastatin, atorvastatin, pitavastatin and rosuvastatin in their lactonized and dihydroxy open acid forms and the pharmaceutically acceptable salts thereof.

13. A method for screening a statin to determine if human metabolic glucuronidation to form an acyl glucuronide conjugate of the open-acid form of the statin is susceptible to inhibition by a co-administered non-statin drug that is metabolically glucuronidated by a UGT isozyme selected from the group consisting of UGT1A1, UGT1A3 and UGT1A10, comprising testing the statin in a UGT-specific glucuronidation assay employing human recombinant UGT1A1, UGT1A3 and UGT1A10, to determine if the statin is metabolically glucuronidated by any of the UGT isozymes.

14. The method of claim 13, wherein the statin is selected from lovastatin, simvastatin, fluvastatin, atorvastatin, pitavastatin and rosuvastatin in their lactonized and dihydroxy open acid forms and the pharmaceutically acceptable salts thereof.

* * * * *